United States Patent
Shen et al.

(10) Patent No.: US 12,100,151 B2
(45) Date of Patent: *Sep. 24, 2024

(54) DROPLET IMAGING PIPELINE

(71) Applicant: Xilis, Inc., Durham, NC (US)

(72) Inventors: Xiling Shen, Chapel Hill, NC (US);
Zhaohui Wang, Chapel Hill, NC (US);
William Quayle, Madison, WI (US);
Garrett Jenkinson, Durham, NC (US)

(73) Assignee: Xilis, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/419,291

(22) Filed: Jan. 22, 2024

(65) Prior Publication Data

US 2024/0153081 A1    May 9, 2024

Related U.S. Application Data

(63) Continuation of application No. 18/235,175, filed on Aug. 17, 2023.
(Continued)

(51) Int. Cl.
*G06T 7/00* (2017.01)
*G01N 1/30* (2006.01)
(Continued)

(52) U.S. Cl.
CPC ............ *G06T 7/0012* (2013.01); *G01N 1/30* (2013.01); *G01N 33/5014* (2013.01); *G06T 7/11* (2017.01);
(Continued)

(58) Field of Classification Search
CPC ......... G06T 7/0012; G06T 7/11; G06T 7/155; G06T 2207/10056; G06T 2207/10064;
(Continued)

(56) References Cited

U.S. PATENT DOCUMENTS 11,494,907 B2    11/2022    Dogdas et al.
11,531,844 B2    12/2022    Bharti et al.
(Continued)

FOREIGN PATENT DOCUMENTS

WO    WO 2022/115433    6/2022

OTHER PUBLICATIONS

Wang et al., "Rapid tissue prototyping with micro-organospheres", Stem Cell Reports, vol. 17, Sep. 13, 2022, pp. 1-17 (Year: 2022).*
(Continued)

*Primary Examiner* — Ping Y Hsieh
*Assistant Examiner* — Jose M Torres
(74) *Attorney, Agent, or Firm* — Fish & Richardson P.C.

(57) ABSTRACT

Methods, systems, and apparatus for an imaging-based MicroOrganoSphere drug assay. In one aspect, a method includes obtaining image data of a well plate comprising a plurality of MicroOrganoSpheres; in response to applying a machine learning model configured to identify instances of at least some of the plurality of MicroOrganoSpheres in the image data, obtaining (i) indications indicative of each instance of the MicroOrganoSpheres and (ii) attributes of each instance of the MicroOrganoSpheres; and normalizing, based on the indications and the attributes, a well-to-well variation in the well plate.

31 Claims, 10 Drawing Sheets

Related U.S. Application Data

(60) Provisional application No. 63/398,797, filed on Aug. 17, 2022.

(51) Int. Cl.
    *G01N 33/50*         (2006.01)
    *G06T 7/11*           (2017.01)
    *G06T 7/155*         (2017.01)

(52) U.S. Cl.
CPC ........ *G06T 7/155* (2017.01); *G01N 2001/302* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01); *G06T 2207/30096* (2013.01)

(58) Field of Classification Search
CPC . G06T 2207/20081; G06T 2207/20084; G06T 2207/30024; G06T 2207/30096; G01N 1/30; G01N 33/5014; G01N 2001/302
See application file for complete search history.

(56) References Cited

U.S. PATENT DOCUMENTS

| | | | |
|---|---|---|---|
| 11,555,180 | B2 | 1/2023 | Shen et al. |
| 11,561,178 | B2 | 1/2023 | Kannan et al. |
| 11,741,604 | B2 | 8/2023 | Kapur et al. |
| 2008/0319679 | A1 | 12/2008 | Li et al. |
| 2020/0218874 | A1 | 7/2020 | Koh et al. |
| 2020/0302241 | A1 | 9/2020 | White et al. |
| 2020/0377861 | A1 | 12/2020 | Shen et al. |
| 2021/0172931 | A1* | 6/2021 | Larsen ............ G06T 7/0012 |
| 2021/0285054 | A1 | 9/2021 | Shen et al. |
| 2021/0325308 | A1 | 10/2021 | Kannan et al. |
| 2022/0138945 | A1 | 5/2022 | Luengo et al. |
| 2022/0392640 | A1* | 12/2022 | Salahudeen ...... G01N 33/57415 |
| 2023/0003716 | A1 | 1/2023 | Shen et al. |
| 2023/0036156 | A1 | 2/2023 | Ho et al. |
| 2024/0062365 | A1 | 2/2024 | Shen et al. |

OTHER PUBLICATIONS

Gritti et al., "MOrgAna: accessible quantitative analysis of organoids with machine learning", The Company of Biologists, Development (2021) 148, pp. 1-8 and Supplementay information (Year: 2021).*
bitbucket.org [online], "FourierDist," Dec. 13, 2021, retrieved on Nov. 17, 2023, retrieved from URL<https://bitbucket.org/biomag/fourierdist/src/master/>, 2 pages.
Borten et al., "Automated brightfield morphometry of 3D organoid populations by OrganoSeg," Scientific Reports, Mar. 2018, 8(1):5319, 10 pages.
Bradski, "The OpenCV Library," Dr. Dobb's Journal, Nov. 2000, 25(11):120-125.
darwin-microfluidics.com [online], "Microfluidic Droplet Generators," available on or before Oct. 2022, via Internet Archive Wayback Machine URL <http://web.archive.org/web/20231115163039/https://darwin-microfluidics.com/collections/microfluidic-droplet-generators?page=2>, retreived on Nov. 15, 2023, URL<https://darwin-microfluidics.com/collections/microfluidic-droplet-generators?page=2, 3 pages.
Dekkers et al., "High-resolution 3D imaging of fixed and cleared organoids," Nature Protocols, Jun. 2019, 14(6):1756-1771.
Ding, et al., "Patient-derived micro-organospheres enable clinical precision oncology," Cell Stem Cell, Jun. 2, 2022, 29(6), 21 pages.
dropletex.com [online], "Droplet Microfluidics," 2023, retrieved on Nov. 15, 2023, retrieved from URL<https://dropletex.com/?gclid=Cj0KCQjwmPSSBhCNARIsAH3cYgZUarfyfALWYq0xQOoGVtWzVksg7hTrvxUJwo2ZmYqzAGCWsM0we68aAvRCEALw_wcB>, 4 pages.

fluigent.com [online], "Microfluidics for Droplet Generation, The science of flow control for emulsion and particle production," available on or before May 24, 2022, via Internet Archive: Wayback Machine URL<http://web.archive.org/web/20231115161806/https://www.fluigent.com/research/applications/droplet-particle-generation/>, retrieved on Nov. 15, 2023, URL<https://www.fluigent.com/research/applications/droplet-particle-generation/?gclid=Cj0KCQjwmPSSBhCNARIsAH3cYgYVDLY-qNhxVS6oCBdV6X3ykGjlee8aPRo87Y9TYvTPgSztPYB76BAaAh0cEALw_wcB>, 25 pages.
Hannah et al., "CellTiter-Glo™ luminescent cell viability assay: A sensitive and rapid method for determining cell viability," Promega Cell Notes, Jan. 2001, 2, pp. 11-13.
He et al., "Mask R-CNN," 2017 IEEE International Conference on Computer Vision, Venice, Italy, Oct. 22-29, 2017, pp. 2980-2988.
He et al., "Deep Residual Learning for Image Recognition," 2016 IEEE Conference on Computer Vision and Pattern Recognition, Las Vegas, Nevada, USA, Jun. 27-30, 2016, pp. 770-778.
Hirling et al., "Cell segmentation and representation with shape priors," Computational and Structural Biotechnology Journal, Jan. 2023, 21:742-750.
Hirling et al., "Fully Automatic Cell Segmentation with Fourier Descriptors," bioRxiv, Dec. 2021, 6 pages.
Jiang et al., "An Automated Organoid Platform with Inter-organoid Homogeneity and Inter-patient Heterogeneity," Dec. 22, 2020, Cell Reports Medicine 1:100161, 18 pages.
Kirillov et al., "PointRend: Image Segmentation as Rendering," 2020 IEEE/CVF Conference on Computer Vision and Pattern Recognition, Seattle, Washington, USA, Jun. 13-19, 2020, pp. 9796-9805.
Langer et al., "Rapid Production and Recovery of Cell Spheroids by Automated Droplet Microfluidics," SLAS Technology, Apr. 2020, 25(2):111-122.
Lin et al., "Feature Pyramid Networks for Object Detection," 2017 IEEE Conference on Computer Vision and Pattern Recognition, Honolulu, Hawaii, USA, Jul. 21-26, 2017, pp. 936-944.
Mohamed, et al., "An integrated microfluidic flow-focusing platform for on-chip fabrication and filtration of cell-laden microgels," Lab Chip, Mar. 2019, 19:1621-1632.
precigenome.com, [online], "iFlow™ Droplet Generation System w. Microfluidic Droplet Generator Chips," 2023, retrieved on Nov. 15, 2023, retrieved from URL< https://www.precigenome.com/microfluidic-droplet-generator?gclid=Cj0KCQjwmPSSBhCNARIsAH3cYgYItqWW45qWRKqflxPGPnfH-5A8AlJjzgwE4hQSlg6H3RGcyj9x2GYaAvBkEALw_wcB>, 9 pages.
Riaz et al., "FourierMask: Instance Segmentation using Fourier Mapping in Implicit Neural Networks," cs.CV, Submitted on Mar. 17, 2022, arXiv:2112.12535, 12 pages.
store.micronit.com [online], "Micronit," 2020, retrieved on Nov. 15, 2023, retrieved from URL< https://store.micronit.com>, 1 page.
Gritti et al., "MOrgAna: accessible quantitative analysis of organoids with machine learning," Development, Sep. 2021, 148(18), 8 pages.
Haan et al., "Deep-Learning-Based Image Reconstruction and Enhancement in Optical Microscopy," IEEE, Nov. 2019, 108(1):30-50, 21 pages.
Hira et al., "From Differential Stains to Next Generation Physiology: Chemical Probes to Visualize 20 Bacterial Cell Structure and Physiology," Molecules, Oct. 2020, 25(21), 4949, 28 pages.
International Search Report and Written Opinion in International Appln. No. PCT/US2023/030455, mailed on Feb. 20, 2024, 14 pages.
Kao et al., "In vitro assessment of the biocompatibility of chemically treated silicone materials with human lens epithelial cells," Scientific Reports, Mar. 2022, 12:4649, 9 pages.
Manini et al., "Synoptic determination of living/dead and active/dormant bacterial fractions in marine sediments," FEMS Microbiology Ecology, Mar. 2005, 55(3):416-423.
Monteiro et al., "Using flow cytometry for mitochondrial assays," MethodsX, 2020, 7, 100938, 9 pages.

* cited by examiner

DROPLET IMAGING PIPELINE

CROSS-REFERENCE TO RELATED APPLICATIONS

This application is a continuation of U.S. application Ser. No. 18/235,175, filed Aug. 17, 2023, now allowed, which claims priority from U.S. Provisional Application No. 63/398,797, filed on Aug. 17, 2022, both of which are incorporated by reference in its entirety.

TECHNICAL FIELD

The present disclosure is directed to systems and methods for performing imaging-based MicroOrganoSphere (MOS) drug assays. Specifically, described herein are systems and methods for identifying instances of MOSs by using a machine learning model and determining drug responses of the instances of MOSs.

BACKGROUND

Immortalized cell lines and genetically engineered mice have been the cornerstone for functional assays in past decades. Recent advances in the development of in vitro 3D tissue models have offered important scientific advantages for disease modeling, regenerative medicine development, drug discovery and toxicities studies, and functional precision medicine. Among them, induced pluripotent stem cell (iPSC) and adult stem cell derived organoids have rapidly emerged as valuable in vitro 3D tissue models for studying human diseases and host-pathogen interaction, because organoids recapitulate the architecture and phenotype of their host tissue in many key ways, thus presenting the potential to yield novel insights and evaluate potential therapeutics.

MicroOrganoSpheres (MOSs) are droplets—typically spheres (or substantially spherical)—made of a base material (e.g. Matrigel or any suitable hydrogel). MOSs can contain one or more three-dimensional cell aggregates formed from groups or clusters of dissociated primary cells distributed within the MOS (including potentially heterogeneous cell clusters). These groups of cells are sometimes referred to as organoids, or as "tumorspheres" in the context of cancer studies. The MicroOrganoSpheres can be patient-derived, also referred to as patient-derived MicroOrganoSpheres (PMOSs). PMOSs have a diameter of between about 50 µm and about 500 µm. In the emerging field of functional precision medicine, PMOSs models have been shown to correlate with clinical outcomes.

Compared to patient-derived xenograft and bulk organoids, PMOSs offer higher rates of establishment and throughput and are less time consuming. PMOSs responses to therapies, such as drug responses, chemotherapy, and radiation therapy, could serve as avatars for therapeutic decision making. However, among the challenges for using PMOS in a clinical setting are tissue heterogeneity, excessive well-to-well variations in a plate, and difficulty of plating consistent number of cells and enforcing uniform growth rate in each PMOS. These difficulties complicate the interpretation of drug responses.

SUMMARY

This specification describes techniques for performing imaging-based MicroOrganoSphere (MOS) drug assays that overcome tissue heterogeneity and well-to-well variations. In particular, techniques that can identify MOSs from imaging of the plate and determine different attributes of MOSs, e.g., a total surface area and a fluorescence activity such as a live cell dye signal and a dead cell dye signal, are useful in determining more reliable drug responses for personalized medicine.

In an aspect, a computer-implemented method includes obtaining image data of a well plate comprising a plurality of MicroOrganoSpheres. The method includes obtaining (i) indications of each instance of the MicroOrganoSpheres and (ii) attributes of each instance of the MicroOrganoSpheres, in response to applying a machine learning model configured to identify instances of at least some of the plurality of MicroOrganoSpheres in the image data. The method includes normalizing, based on the indications and the attributes, a well-to-well variation in the well plate.

In an aspect, a computer-implemented method includes, for each MicroOrganoSphere of a plurality of MicroOrganoSpheres, obtaining a first input including brightfield image data and fluorescence image data and obtaining a second input indicative of a ground-truth label representing each MicroOrganoSphere instance. The method includes training, by using a set of the first and the second inputs across the plurality of MicroOrganoSpheres, a machine learning model configured to identify (i) each instance of the MicroOrganoSpheres and (ii) attributes of each instance of the MicroOrganoSpheres.

Embodiments of the methods described above can include one or any combination of two or more of the following features.

The methods may include performing a drug assay on the plurality of MicroOrganoSpheres, where the drug assay measures cell viability in response to a drug treatment to a given well in the well plate, and determining the cell viability in the normalized well plate. The cell viability measured by the drug assay can be adjusted using the attributes of MOSs, e.g., a total surface area. The MicroOrganoSpheres may be derived from a patient-derived tissue sample, e.g., a biopsy sample from a metastatic tumor and a clinical tumor sample comprising both cancer cells and stromal cells. The image data include a brightfield image and a fluorescence image of the well plate. The brightfield image and the fluorescence image of the well plate are collected using an imaging device, e.g., imaging cytometer. The indications include a visual representation of each instance of the MicroOrganoSpheres in the image data. The attributes of each instance of the MicroOrganoSpheres include a total surface area of each instance, a live cell dye signal, and a dead cell dye signal. In some implementations, obtaining the image data of the well plate includes obtaining the image data for one or more wells in the well plate at a single focal plane. In some implementations, obtaining the image data of the well plate includes using a two-dimensional projection of three-dimensional confocal microscopy Z-stacks.

The methods may include displaying the visual representation of each instance of the MicroOrganoSpheres on a user interface. Obtaining the indications of each instance of the MicroOrganoSpheres in the image data can include generating a corresponding mask represented using a Fourier series representation, wherein the Fourier series representation is generated based on coefficients output by the machine learning model. The methods may include determining, based on the indications outputted by the machine learning model, a fluorescence activity of one or more instances of the MicroOrganoSpheres. The fluorescence activity includes a live cell dye signal and a dead cell dye signal of the one or more instances of the MicroOrganoSphere. Determining the fluorescence activity of the one or more instances of the MicroOrganoSpheres includes performing a logical operation between the image data and the indications.

The methods may include iteratively adjusting the indications outputted from the machine learning model such that the dead cell dye signal is captured and outputting, based on the adjusted indications, the fluorescence activity of the one or more instances of the Micro Organo Spheres.

Normalizing the well-to-well variation in the well plate includes obtaining a total surface area of each instance of the MicroOrganoSpheres in the well plate, where the total surface area is correlated with a level of adenosine triphosphate (ATP) of each instance of the MicroOrganoSpheres; obtaining, for each well of the well plate, a cell viability in response to a drug treatment; and adjusting, based on the total surface area, respective cell viability across a plurality of wells in the well plate.

The methods can include treating one or more wells in the well plate with a stain (e.g., Invitrogen™ CellTracker™ Deep Red dye) that non-specifically binds to organic tissue and a base material of a MicroOrganoSphere. For example, this treatment could take place prior to obtaining the first input including brightfield image data and fluorescence image data. The methods can include treating a given well, in the well plate, with a live cell dye and a dead cell dye; performing a drug assay on a plurality of MicroOrganoSpheres in the given well; and determining an integrated cell viability in the given well. The drug assay can include a CellTiter-Glo (CTG) luminescent cell viability assay. The live cell indicators can include a Calcein-AM (CAM) or a mitotracker viewer dye. The dead cell indicators can include an ethidium homodimer (EtH), e.g., EtH-2, or fluorescent conjugates of annexin V. The methods can include determining, based on the integrated cell viability and fluorescence imaging signals, cytotoxic or cytostatic drug responses. The methods can include, in response to applying a size filter to the indications, filtering out stromal cells and non-tumorspheres in the indications, where the size filter removes cells under a pre-defined size from the indications.

The methods can include, in response to determining that a saturation level of the fluorescence image data does not meet a pre-defined threshold, applying binarization to the fluorescence image data. Training the machine learning model can include providing the set of the first and the second inputs to a Mask-RCNN architecture, wherein the Mask-RCNN architecture includes a plurality of convolutional neural networks and a feature pyramid network. Alternatively, training the machine learning model can include training a neural network to output coefficients for a Fourier series representation of one or more image segmentation masks (e.g., image instance segmentation masks) corresponding to the MicroOrganoSpheres. In some implementations, the machine learning model can be trained using images that include labeled MicroOrganoSphere instances, the labeled MicroOrganoSphere instances being labeled using a pre-trained neural network configured to generate image segmentation masks (e.g., image instance segmentation masks). The images that include the labeled MicroOrganoSphere instances can be generated from unlabeled images, wherein the unlabeled images are pre-processed using at least one of (i) a mathematical transformation that enhances fluorescence corresponding to stained MicroOrganoSpheres present in the unlabeled images, (ii) a mathematical morphology operation that enhances circular objects that are within a defined range of sizes (e.g., a range of sizes corresponding to potential MOS sizes of about 50 μm to about 500 μm), and (iii) an image-resizing operation (e.g., to ensure the MOSs are of sizes compatible with objects detectable by the pre-trained neural network such as objects used to train the pre-trained neural network). Alternatively, or in addition, the unlabeled images can first be pre-processed using one or more filters (e.g., a median filter) to remove noise signals.

Other embodiments of this aspect include corresponding computers systems, apparatus, and computer programs recorded on one or more computer storage devices, each configured to perform the operations of the methods described herein. Embodiments include a system of one or more processors and one or more storage devices storing instructions that are operable, when executed by the one or more processors, to cause the one or more processors to perform the operations. Embodiments also include a non-transitory computer-readable medium, including software instructions, that when executed by a computer, cause the computer to execute the operations.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
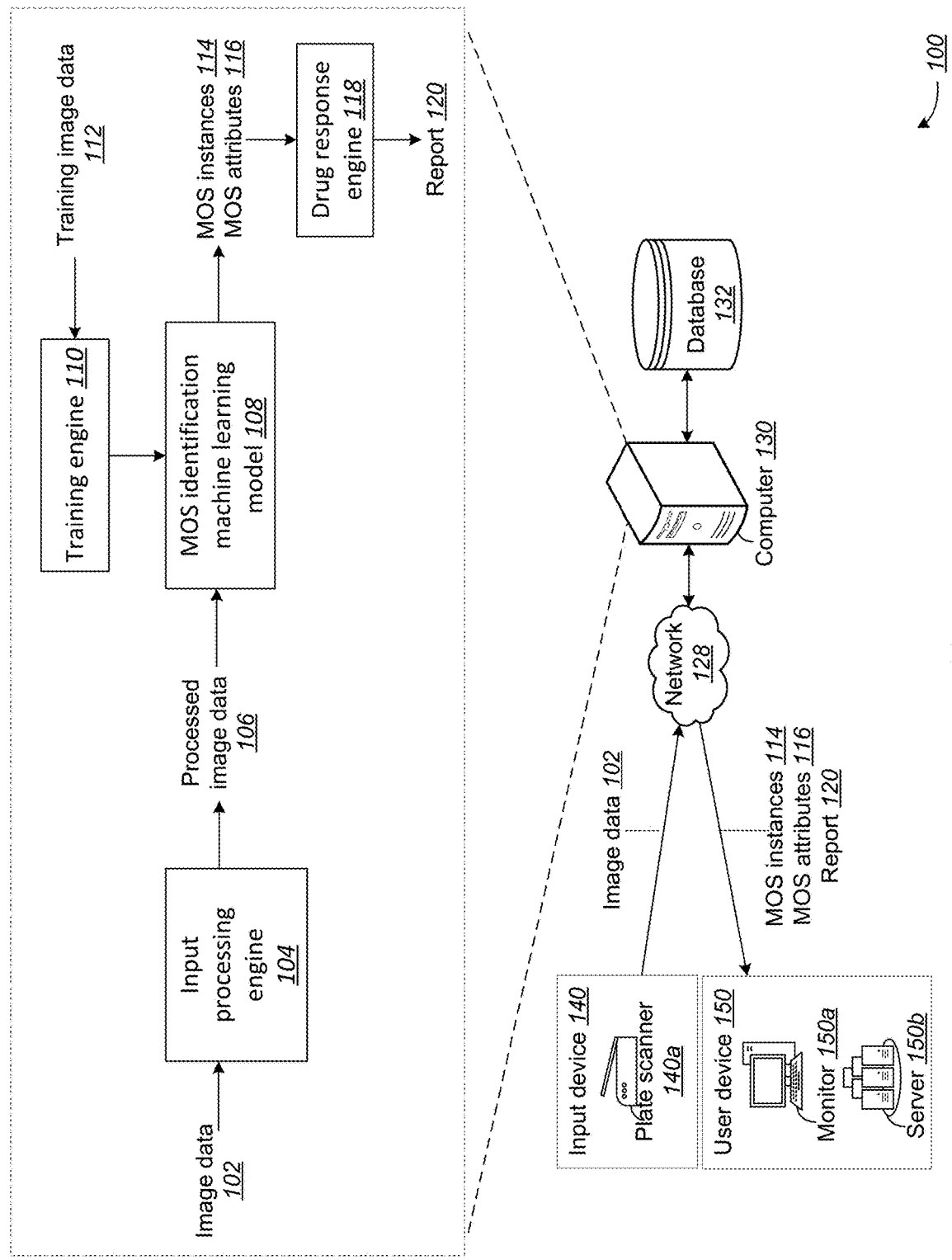
FIG. 1 is a block diagram of an example system for performing an imaging-based MicroOrganoSphere (MOS) drug assay.

The systems and methods described here relate to an approach to performing imaging-based MicroOrganoSphere (MOS) drug assay. For instance, the systems and methods described here aim to identify instances of MOSs in image data, e.g., brightfield image of a plate, and determine attributes of MOSs including a total surface area, a proportion of live cells, and a proportion of dead cells in each MOS instance. Referring to image data 102 (of FIG. 1), while this disclosure describes MOS imagery, other image data, e.g., structures with a similar size, surface to volume ratio, and/or characteristics that enable imaging at a single plane (e.g., widefield imaging or suitable two-dimensional projections of Z-stack confocal imaging), can be processed similarly.

The system and methods of the present disclosure can have one or more of the following advantages. The machine learning approaches described here enable, in a computationally efficient manner, automatically identifying MOSs and using such information in drug response analyses. The manually identifying MOSs from the image data is laborious, time-consuming, and relatively unreliable. This computational efficiency is important to provide timely feedback on personalized medicine, e.g., which drug is likely to be effective for a patient. In addition, the attributes of MOSs can be used to account for tissue heterogeneity and well-to-well variations in a plate, enabling interpretable, reliable drug responses. Furthermore, identified resistant clones can be used to study the drug resistance mechanism and to develop a screening of the resistant population for a therapeutic recommendation when the disease recurs. Merely by way of example, resistant clones can be isolated, and one or more of genetic, transcriptomic, and proteomic analysis can be performed, in order to understand the drug resistance mechanism. In addition, responses of MOS to one or more drugs tested can be used to determine which drug or combinations of drugs should be used or not used to treat a patient based on test results.

Identifying MOSs from imaging of the plate can also have several advantages compared to, for example, identifying clusters of cells (e.g., tumorspheres) directly. First, because MOSs tend to fall to the bottom of the well, they can be imaged at a single focal plane or using a two-dimensional projection rather than using full three-dimensional Z-stack confocal imaging to capture images at multiple focal distances. Second, because multiple MOSs in a single well provide individual micro-environments that have little to no influence on one another, the presence of multiple MOSs in a single well (e.g., a well that is treated with a particular set of conditions) can allow for observing each MOS as a separate experiment, effectively multiplying the number of experiments a researcher can perform in a given time period. Third, since MOSs are made with a hydrogel base material, they enable the use of different imaging stains (e.g., Invitrogen™ CellTracker™ Deep Red dye) that bind non-specifically to the base material of the MOS rather than binding specifically to the tumorsphere (or organoid) tissue. Fourth, since MOSs tend to be more spherical than irregularly shaped tumorspheres (or organoids), machine learning models for identifying MOSs can be adapted to take advantage of this prior knowledge to improve detection capabilities and/or require less training data to achieve similar performance as machine learning models trained to identify tumorspheres (or organoids) directly.

FIG. 1 is a block diagram of an example system 100 for performing an imaging-based MOS drug assay. The system 100 obtains image data 102 and generates MOS instances 114 and MOS attributes 116. In some implementations, the system 100 generates a report 120 summarizing drug responses and recommending a particular drug for a patient. The system 100 includes an input device 140, a network 128, and one or more computers 130 (e.g., one or more local or cloud-based processors, one or more servers). The computer 130 can include an input processing engine 104, a MOS identification machine learning model 108 that can be trained by a training engine 110, and a drug response engine 118. For purposes of the present disclosure, an "engine" can include one or more software modules, one or more hardware modules, or a combination of one or more software modules and one or more hardware modules. In some implementations, one or more computers are dedicated to a particular engine. In some implementations, multiple engines can be installed and executed on the same computer or computers.

The input device 140 is a device that is configured to obtain the image data 102, a device that is configured to provide image data 102 to another device across the network 128, or any suitable combination thereof. For example, the input device 140 can include a plate scanner 140a that is configured to scan the plate and output the image of the plate in a format (e.g., tiff format). In some implementations, the image data 102 is brightfield image of MOSs. In some implementations, the image data is fluorescence image of MOSs. In some implementations, the image data 102 is a combination of brightfield and fluorescence images of MOSs. In some implementations, the image data 102 include images of structures with similar size and/or surface to volume ratios to MOSs. In some implementations, the structures have a particular characteristic that enable them to be imagined at a single plane, e.g., structures formed using a droplet-based microfluidic device. Prior to obtaining the image data 102, the MOSs can be stained, for example, by treating one or more wells in a well plate that the MOS are in, with a stain that non-specifically binds to organic tissue and a base material of a MicroOrganoSphere (e.g., Matrigel). One example of such a stain is Invitrogen™ CellTracker™ Deep Red dye, which contributes to the diffuse glow of the MOSs in the image data 102 and has been found to bind well to a wide variety of MOSs (e.g., showing robustness to variations in the base material). While the diffuse glow of stains such as Invitrogen™ CellTracker™ Deep Red dye have previously made them unattractive candidates for staining organoids or tumorspheres directly, this diffuse glow has been found to be highly effective for MOS detection, especially when combined with image pre-processing operations, as described in further detail below.

The computer 130 can access the image data 102, e.g., stored in a cloud server, via the network 128. The network 128 can include one or more of a wired Ethernet network, a wired optical network, a wireless WiFi network, a LAN, a WAN, a Bluetooth network, a cellular network, the Internet, or other suitable network, or any combination thereof.

The computer 130 is configured to obtain the image data 102 from the input device 140. In some implementations, the image data 102 can be data received over the network 128. In some implementations, the computer 130 can store the image data 102 in a database 132 and access the database 132 to retrieve the image data 102. The database 132, e.g., a local database or a cloud-based database, can store the image data 102 in a standardized format for a rapid processing of images.

The input processing engine 104 is configured to receive the image data 102 and generate processed imaged data 106 for input to the MOS identification machine learning model 108. The input processing engine 104 can perform standardization of a format of the image data 102, encryption of the image data 102 to comply with the privacy requirement, or other data processing. For example, the input processing engine 104 can perform a variety of image pre-processing operations including filtering, mathematical morphology operations, mathematical transformations, and/or image-resizing operations (in any order). With respect to filtering, median filtering can be implemented to reduce noise signals. With respect to mathematical morphology operations, the input processing engine 104 can enhance disk-like objects that are within a defined range of sizes in the image data 102 while suppressing non-circular or improperly sized objects (e.g., thereby increasing the likelihood of specifically recognizing the nearly spherical MOS droplets included in the image data 102). With respect to mathematical transformations, various transformations including power transformations, square root transformations, cube root transformations, logarithmic transformations, etc. can be implemented to enhance the fluorescence in the image data 102 that corresponds to the diffuse glow of the stained MOSs. In some cases, this fluorescence may be a "middle-level fluorescence" that is less intense than the fluorescence corresponding to dyes that bind specifically to the tumorspheres (or other organoids), but more intense than the background of the image. In some cases, the images in the image data 102 can be resized to be larger or smaller so as to ensure the size of the stained MOSs are on the same order of magnitude as the size of the imaged objects used to train the pretrained neural network. This image-resizing can increase the accuracy of the neural network in creating instance segmentation labels. In some implementations, the input processing engine 104 performs binarization for the fluorescence images in the training data that were not fully saturated, or conversely, to limit the range of values to an intermediate range of intensities. For example, the input processing engine 104 can perform binarization for a fluorescence image by computing a saturation offset and setting each pixel of the fluorescence image such that the fluorescence image is properly saturated, e.g., setting to maximum if a given pixel's intensity is larger than a pre-defined threshold and setting to minimum if a given pixel's intensity is smaller than the pre-defined threshold.

Figures 3A, 3B:
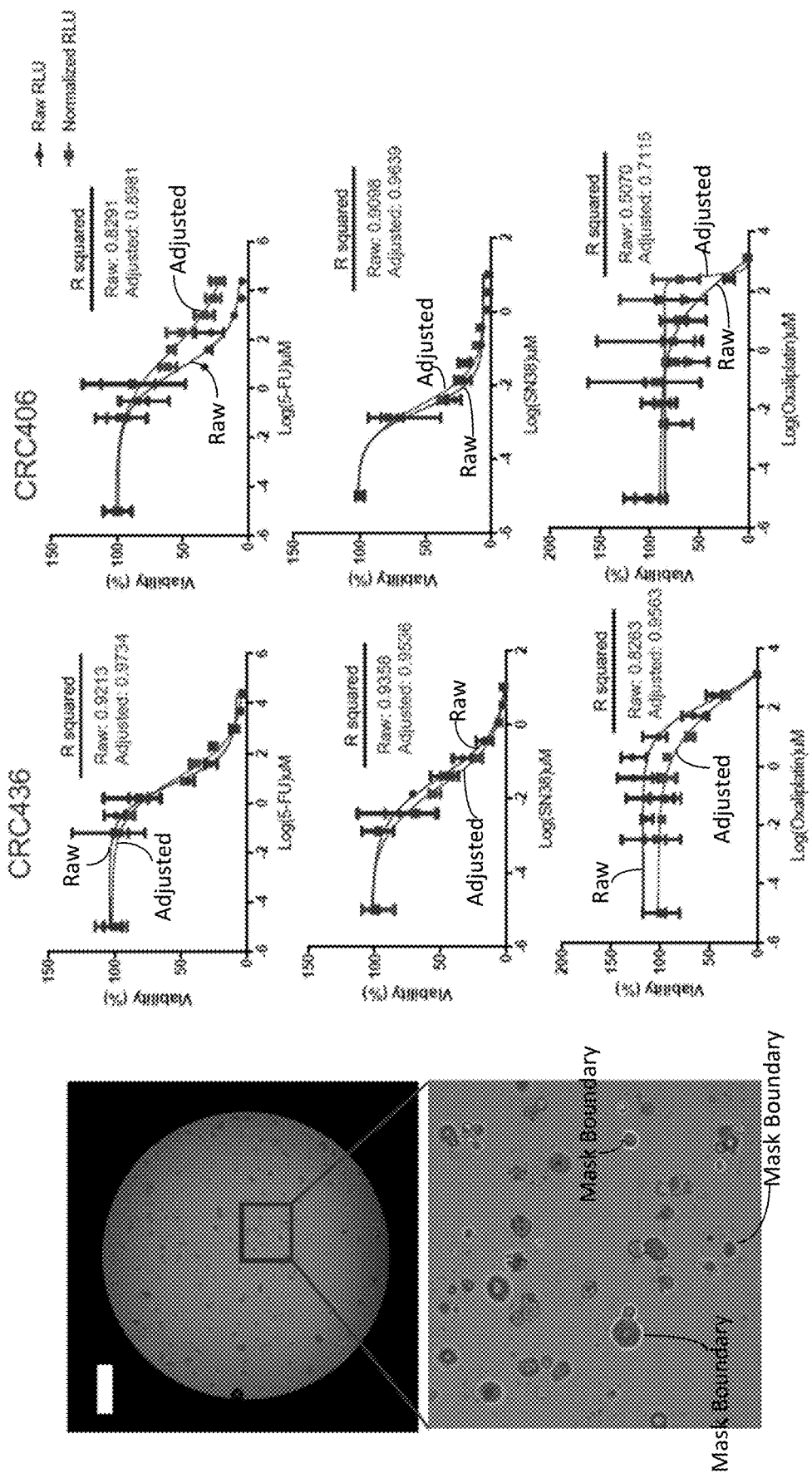
FIG. 3A illustrates an example image of a whole well scanning (top panel) and a zoom-in view (bottom panel) showing MOS instances identified by a machine learning method.
FIG. 3B illustrates example drug response curves of CRC436 and CRC406 MOSs before and after normalization.

The processed image data 106 generated by the input processing engine 104 can include a data structure that represents pixels of scanned plate images, e.g., an image of a whole well scanning as shown in FIG. 3A. The processed image data 106 outputted by the input processing engine 104 is provided as an input to the MOS identification machine learning model 108. In some implementations, the MOS identification machine learning model 108 receives the image data 102 without the image processing step by the input processing engine 104.

The MOS identification machine learning model 108 is configured to receive the processed image data 106 and generate MOS instances 114, MOS attributes 116, or both. The MOS instances 114 represent individual instances of MOSs in the image data. The MOS attributes 116 can include a total surface area and optionally live/dead cell dye signals. The live/dead cell dye signals can be applicable if the image data 106 include fluorescence images treated with a live cell dye and a dead cell dye. The MOS identification machine learning model 108 is a model outputted from a training engine 110.

The training engine 110 obtains training image data 112 and processes the training image data 112 to train and output the MOS identification machine learning model 108. The training image data 112 include multiple paired images including brightfield image data and fluorescence image data. Each of the training image data 112 is labeled such that each MOS instance is annotated. This ground-truth label can be derived by manually annotating disjoint active regions from the fluorescence images, or it can be derived automatically by a pre-trained neural network as described in further detail below. In some implementations, the training image data 112 are processed using the input processing engine 104 as described referring to FIG. 1 (or by a different engine that performs one or more similar operations). By using the training image data 112, the training engine 110 trains a machine learning model configured to identify and segment each instance of the MOSs and attributes of each instance of the MOSs by processing the training image data 112 through multiple layers. Additional details about training the MOS identification machine learning model 108 are described in relation to FIG. 6.

Figure 6:
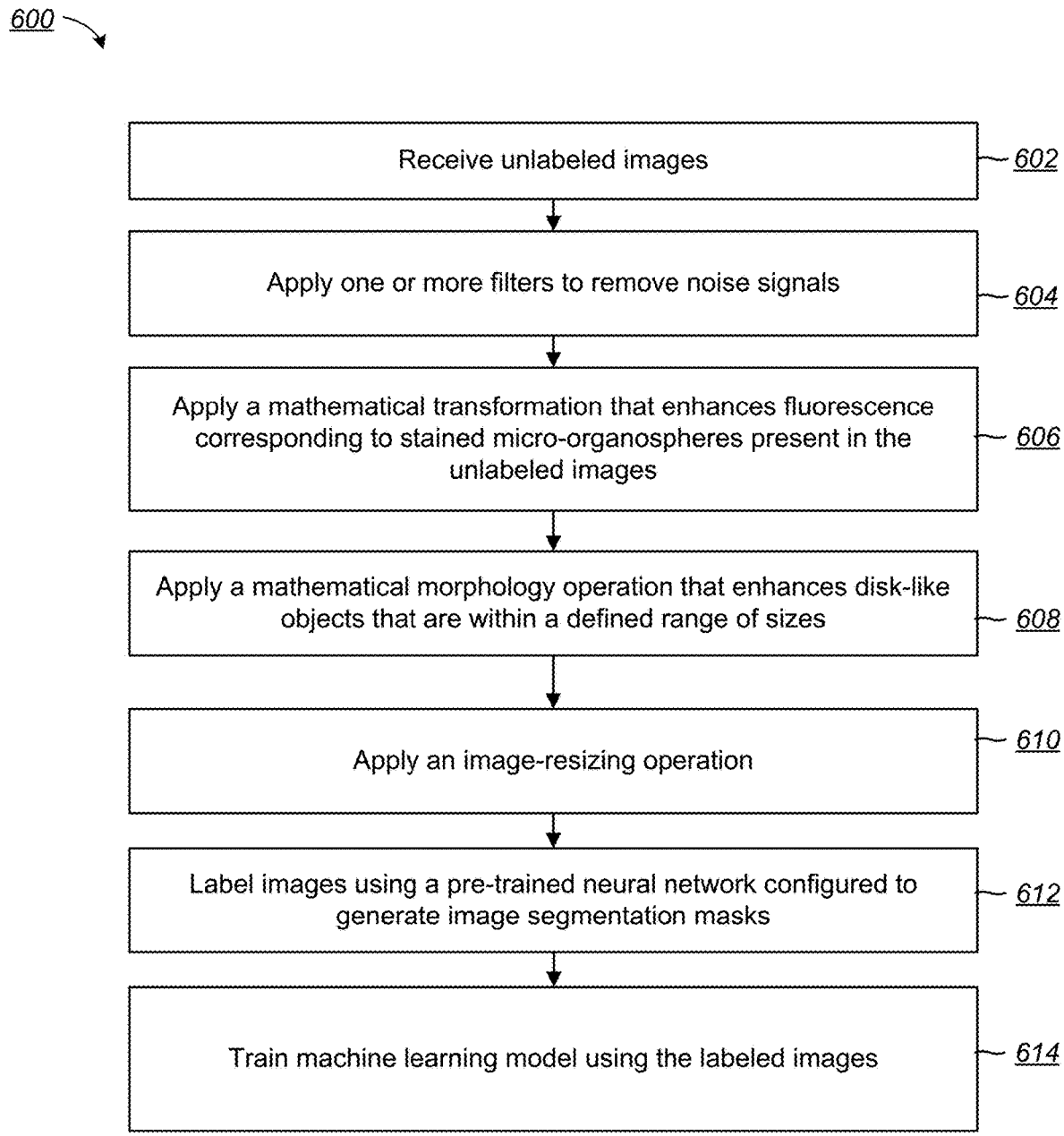
FIG. 6 is a flowchart of an example process for training a machine learning model used for performing imaging-based MOS drug assays.

FIG. 6 is a flowchart of an example process 600 for training a machine learning model used for performing imaging-based MOS drug assays (e.g., the MOS identification machine learning model 108). Operations of the process 600 include receiving unlabeled images (602). For example, the unlabeled images can be brightfield image data and fluorescence image data of stained MOSs that have not yet been labeled with any indications of the location, size, or shape of the MOSs. Operations of the process 600 also include applying one or more filters (e.g., a median filter) to remove noise signals (604); applying a mathematical transformation that enhances fluorescence corresponding to stained MicroOrganoSpheres present in the unlabeled images (606); applying a mathematical morphology operation that enhances disk-like objects that are within a defined range of sizes (608); and applying an image-resizing operation (610). Operations 604, 606, 608, 610 are sometimes referred to in this specification as "pre-processing operations" and correspond to the previously described image pre-processing operations performed by the input processing engine 104. Operations 604, 606, 608, 610 can be interchangeable in order, and in some implementations, only a portion of the operations 604, 606, 608, 610 are performed in the process 600.

After pre-processing the unlabeled images, the process 600 includes labelling images using a pre-trained neural network configured to generate image segmentation masks (612). For example, the neural network can be a pre-trained neural network that outputs coefficients for a Fourier series representation of one or more image segmentation masks corresponding to the MOSs (described in further detail below). In this sense, the generated image segmentation masks can be said to have been produced "automatically" by the pre-trained neural network (e.g., without manual annotation), and the masks are then treated as ground-truth labels indicating the location, size, and shape of MOSs in the previously unlabeled images. One example of a pre-trained neural network that can be used for the operation 612 is the "FourierDist" network described in Fully Automatic Cell Segmentation with Fourier Descriptors (17 Dec. 2021) (www.biorxiv.org/content/10.1101/2021.12.17.472408v1) and Cell segmentation and representation with shape priors, Computational and Structural Biotechnology Journal, Vol. 21, 2023, pp. 742-740 (doi.org/10.1016/j.csbj.2022.12.034), which are both hereby incorporated by reference in their entireties, with corresponding source code available at www.bitbucket.org/biomag/fourierdist/src/master/.

Once the images have been labeled with "ground-truth labels," operations of the process 600 include training the machine learning model using the labeled images (614). For example, this can correspond to training the MOS identification machine learning model 108 through a supervised learning approach using the training engine 110. In some implementations, the MOS identification machine learning model 108 can be a similar model to the pre-trained neural network described above, except that its weights are fine-tuned for the detection of MOSs. In addition, the MOS identification machine learning model 108 can be further constrained compared to the pre-trained neural network so that it outputs a smaller, pre-defined number of Fourier series coefficients, thereby biasing the model towards detecting near-circular MOS droplets (and reducing the risk of mistaking irregularly shaped tumorspheres for MOSs).

Referring back to FIG. 1, in some implementations, the machine learning model 108 uses a semantic segmentation algorithm, an instance segmentation algorithm, or a panoptic segmentation algorithm. In some implementations, the machine learning model is implemented in a Mask-RCNN architecture including multiple convolutional neural networks and a feature pyramid network (FPN). An advantage of the Mask-RCNN architecture is that the trained machine learning model outputs a mask indicating which pixels represent part of the MOS and which do not. This mask can be used to determine the fluorescence activity of a given MOS, e.g., by taking a logical operation (e.g., bitwise 'AND') between the mask and the fluorescence image. However, in some instances, Mask-RCNN might require large amounts of training data that may not be accessible, and other machine learning approaches may be desirable.

For example, in some implementations, the MOS identification machine learning model 108 can be implemented using a different neural network-based architecture trained to perform image segmentation and to produce a similar mask as the Mask-RCNN architecture. In one implementation, the MOS identification machine learning model 108 can be a neural network trained to output coefficients for a Fourier series representation of one or more image segmentation masks corresponding to the MOSs. In particular, since it is known a priori that MOSs tend to be nearly spherical, the neural network can be constrained to only output coefficients for a small, pre-defined number of Fourier series coefficients (e.g., since a perfect circle can be represented by just a single Fourier coefficient and since higher levels of complexity are unlikely to be needed). This can reduce the complexity of the neural network, decrease the time needed to analyze images, and reduce the amount of training data needed to train the machine learning model compared to the Mask-RCNN architecture described above. An example implementation of instance segmentation using Fourier mapping in implicit neural networks is described in Fully Automatic Cell Segmentation with Fourier Descriptors (17 Dec. 2021) (www.biorxiv.org/content/10.1101/2021.12.17.472408v1) and Cell segmentation and representation with shape priors, Computational and Structural Biotechnology Journal, Vol. 21, 2023, pp. 742-740 (doi.org/10.1016/j.csbj.2022.12.034), which are both hereby incorporated by reference in their entireties.

In some implementations, the machine learning model can be implemented using one or more other architectures (e.g., U-net, single shot multibox detector (SSD), YOLO, detection transformer (DETR), vision transformer (ViT), etc.). In some implementations, the machine learning model can utilize a modified face recognition algorithm.

The drug response engine 118 is configured to receive the MOS instances 114 and the MOS attributes 116 and generates the report 120. The drug response engine 118 normalizes cell viability measurements, e.g., a CellTiter-Glo (CTG) luminescent cell viability values, across wells. For example, the drug response engine 118 uses total surface areas, MOS counts, or pre-dosing fluorescence integrals within the MOS instances outputted from the machine learning model to normalize the plating variations, e.g., by dividing the cell viability measurements of each well by these surface area ratios. Based on the adjusted cell viability measurements, the drug response engine 118 outputs drug response curves and summarizes a drug recommendation for a patient.

In some implementations for the live and dead cell dyes-based imaging assay, the drug response engine 118 determines a live cell dye signal and a dead cell dye signal. In some implementations, the drug response engine 118 determines ratios of a live cell dye signal and a dead cell dye signal, also referred to as integrated intensities.

The computer 130 can generate rendering data that, when rendered by a device having a display such as a user device 150 (e.g., a computer having a monitor 150a, a server 150b, or another suitable user device), can cause the device to output data including the MOS instances 114 and the MOS attributes 116. Such rendering data can be transmitted, by the computer 130, to the user device 150 through the network 128 and processed by the user device 150 or associated processor to generate output data for display on the user device 150. In some implementations, the user device 150 can be coupled to the computer 130. In such instances, the rendered data can be processed by the computer 130, and cause the computer 130 to display the MOS instances, e.g., visual representations of identified MOSs and summary of their attributes, on a user interface.

Figure 2:
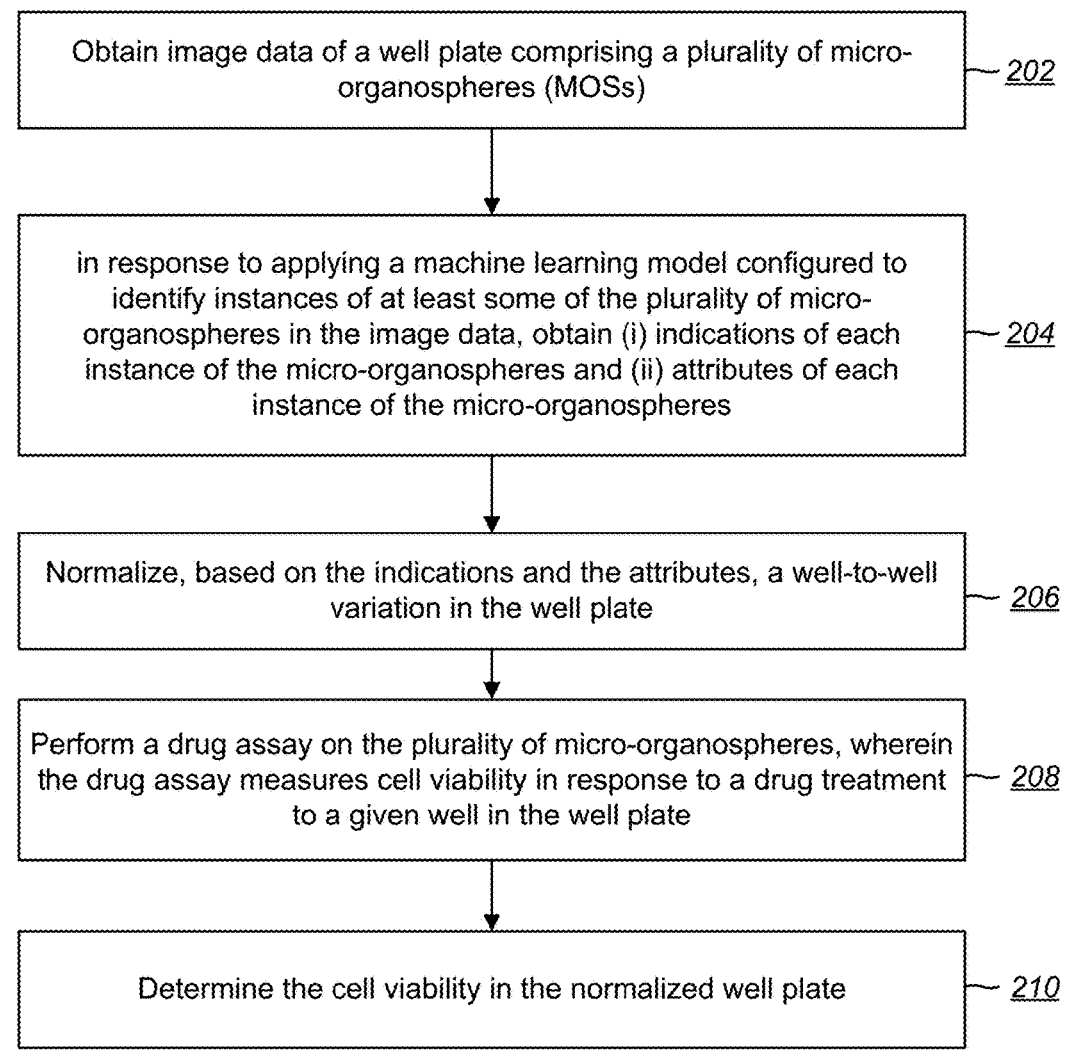
FIG. 2 is a flowchart of example process for performing an imaging-based MOS drug assay.

FIG. 2 is a flowchart of an example of a process 200 for performing imaging-based MOS drug assay. The process will be described as being performed by a system of one or more computers programmed appropriately in accordance with this specification. For example, the computer 130 of FIG. 1 can perform at least a portion of the example process. In some implementations, various steps of the process 200 can be run in parallel, in combination, in loops, or in any order.

The system obtains image data of a well plate comprising a plurality of MicroOrganoSpheres (MOSs) (202). In some implementations, MOSs are derived from a patient-derived tissue sample, e.g., a clinical tumor sample and a biopsy sample from a metastatic tumor. In some implementations, the MOSs are dyed with a stain (e.g., Invitrogen™ Cell-Tracker™ Deep Red dye) that non-specifically binds to organic tissue and a base material of the MOSs. The image data include a brightfield image and a fluorescence image of the well plate. These images are collected using an imaging device, e.g., an imaging cytometer.

The system obtains (i) a mask indicative of each instance of the MicroOrganoSpheres and (ii) attributes, e.g., a total surface area and if applicable, live/dead cell signals, of each instance of the MicroOrganoSpheres, in response to applying a machine learning model (e.g., the MOS identification machine learning model 108) configured to identify instances of at least some of the plurality of MicroOrganoSpheres in the image data (204). In some implementations, the system filters out stromal cells and non-tumorspheres in the mask by using tumor-specific fluorescence stains to generate additional masks that can be intersected with the MOS's masks, potentially in addition to size-filtering of the resulting intersected masks. The mask includes a visual representation of each instance of the MOSs in the image data. In some implementation, the system displays the visual representation of each instance of the MOSs on a user interface, in response to a user request. For example, as shown in FIG. 3A, the user interface indicated each instance of the MOSs with boundaries around the MOSs.

Figure 4C:
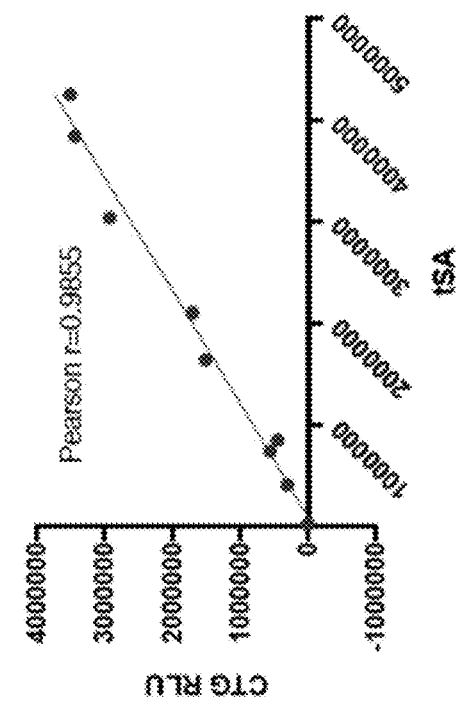
FIGS. 4C-4D illustrate correlations between total surface area (tSA) of MOSs measured by a machine learning method and CTG measurements in relative light unit (RLU).
Figure 4D:
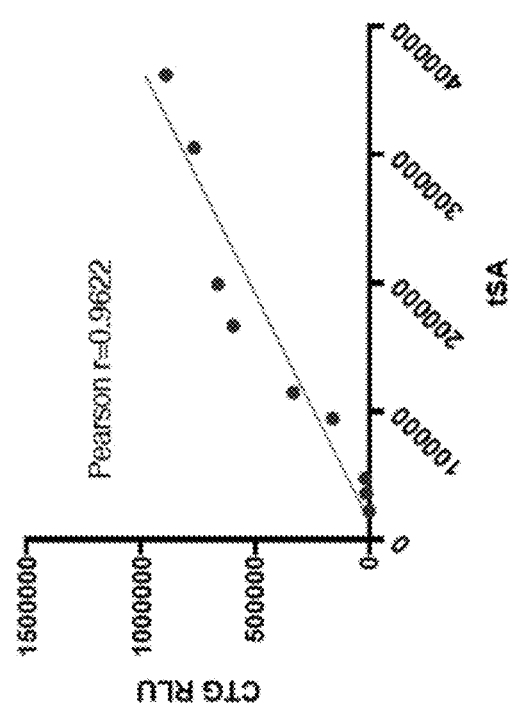

The system normalizes, based on the mask and the attributes, a well-to-well variation in the well plate (206) (e.g., well-to-well variation caused by different numbers of MOSs in each well, MOSs of different sizes in each well, MOSs of differing initial biomass/tumor cell content, etc.). One of the approaches of normalizing the well-to-well variation is based on a total surface area of the MOSs. For example, the system obtains a total surface area of each instance of the MicroOrganoSpheres in the well plate. As shown in FIGS. 4C-4D, the total surface area was shown to be correlated with a level of adenosine triphosphate (ATP) of each instance of the MicroOrganoSpheres. The system obtains, for each well of the well plate, a cell viability in response to a drug treatment and adjusts, based on the total surface area, respective cell viability across a plurality of wells in the well plate. This approach is distinct, compared to relying on a cell viability measured by an absolute number of cells, which is relatively less reliable due to the well-to-well variation.

In some implementations, the system performs a drug assay on the plurality of MicroOrganoSpheres (208). The drug assay, e.g., a CellTiter-Glo (CTG) luminescent cell viability assay, measures cell viability in response to a drug treatment to a given well in the well plate. The system determines the cell viability in the normalized well plate (210). In some implementations, the system determines the cell viability by only considering fluorescence signals that originate from within the boundaries of an identified MOS (e.g., eliminating noise from outside of the MOS, which should not contain any three-dimensional cell aggregates).

In some implementations, the system treats a given well with a live cell dye, e.g., a calcein-AM or a mitotracker viewer, and a dead cell dye, e.g., an ethidium homodimer-2 or a fluorescent conjugated annexin V. After treating the given well, the system performs a drug assay on a plurality of MicroOrganoSpheres in the given well and determines an integrated cell viability in the given well. The integrated cell viability includes information such as a live cell signal indicative of a proportion of live cells in each MOS instance and a dead cell signal indicative of a proportion of dead cells in each MOS instance. In some implementations, the system determines, based on the integrated cell viability, cytotoxic or cytostatic drug responses.

In some implementations, the system determines a fluorescence activity of one or more instances of the MicroOrganoSpheres, based on the mask outputted by the machine learning model. The fluorescence activity includes the live cell dye signal and the dead cell dye signal of the one or more instances of the MicroOrganoSphere. To determine the fluorescence activity, the system performs a bitwise logical operation (e.g., an 'AND' operation) between the image data and the mask. In some implementations, the system iteratively adjusts the mask outputted from the machine learning model such that the dead cell dye signal is captured and outputs, based on the adjusted mask, the fluorescence activity of the one or more instances of the MicroOrganoSpheres.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a standalone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

EXAMPLES

The disclosure provides the following examples, to assist the description of the systems, methodologies, etc. without limiting claim scope.

The following methods were used in the Examples below.

Methods

Brightfield and Fluorescence Imaging of MicroOrganoSpheres (MOSs)

The plates were scanned using the Celigo imaging cytometer and its software. We collected the brightfield images on the day (day 0) of the drug treatment and on the day right before performing the CellTiter-Glo (CTG) assay. Upon inserting the plate, images were set to be acquired on brightfield, green, and red fluorescence channels. The brightfield channel was used to focus the device and ensure the MOS boundaries were crisp. The green (live cell) fluorescence channel exposure time was then adjusted to ensure pixel intensity was below 200 across the control triplicate wells to avoid overexposure. This process was repeated for the red (dead cell) fluorescence channel in the positive control, killing condition triplicate wells. After scanning the plate, the stitched images of each well were exported in tiff format for the downstream imaging analysis.

Live and Dead Cell Dye Staining

We performed the live and dead cell staining on the same day prior to the CTG assay. For 96 well plates, a working dye solution of 20 µM Ethidium Homodimer-2 (Thermo Fisher, Cat. No. E3599) and 5 µM Calcein AM (Thermo Fisher, catalog No. C3100MP) was prepared by adding 1 mM Calcein AM, 1 mM Ethidium Homodimer-2, and CRC media in a 1:8:191 ratio. For 384-well plates, the working dye solution of 10 µM Ethidium Homodimer-2 and 2.5 µM Calcein AM was prepared by adding 1 mM Calcein AM, 1 mM Ethidium Homodimer-2, and colorectal cancer (CRC) media in a 1:8:391 ratio. After the solution was prepared, 11 µL and 10 µL of dye solution were added to each well on the 96-well and 384-wells plates, respectively, to yield a final well concentration of 2 µM Ethidium Homodimer-2 and 0.5 µM Calcein AM. The plates were then incubated for 45 min at 37° C.

Cell Viability Assay

To measure cell viability, we used the CTG luminescent cell viability assay. CellTiter-Glo 3-D reagent (Promega, catalog no. G9681) was added in a 1:1 ratio with the initial well volume (100 or 40111_, of CTG reagent 96-well plates and 384-well plates, respectively). The plates were placed on a shaker for 30 min. We measured luminescence by using a plate reader for each well.

A Machine Learning for Identifying MOSs (Organoid/Tumorspheres)

A machine learning model was trained using the training data of brightfield images of well-established colorectal MOS and paired Calcein-AM fluorescence images, all collected with the Celigo imaging cytometer. In training the machine learning model, the Mask-RCNN implementation in Detectron was utilized. This configuration used a ResNet50 backbone and a feature pyramid network (FPN). Ground-truth labels indicative of MOSs instances were derived from the fluorescence images by identifying each disjoint active region as a separate MOS instance. Since some of the fluorescence images in the training data were not fully saturated, the binarization was performed using a sliding threshold: first, a saturation offset d was computed as 255 minus the maximum pixel value in the fluorescence image; second, a threshold was computed as max(30, 90−d); and finally, each pixel is set to either 255 (if its intensity was larger than this threshold) or 0 (if its intensity was smaller). The machine learning model was trained to the resulting labels for 20 epochs with a learning rate of 0.00025.

For MOSs including both living and dead cells, the dead cells were frequently found on the outer surface of the organoid/tumorsphere or sprinkled around it. As a result, predictions by the machine learning model excluded some fraction of these dead cells. Therefore, in studies involving the ratio of live-cell stain to dead-cell stain, we increased the predicted object mask to capture all the dead-stain fluorescence signal. The size increase was performed using one iteration of the dilate algorithm in OpenCV with a kernel size of 10×10. Any other MOSs detected by the machine learning model that overlap with this expanded region were removed before the integrated fluorescence was computed.

Data Analysis of Imaging-Based Drug Assay Pipeline

Cell viability was assessed using both metabolic and imaging parameters. For the metabolic assay, Day 0 brightfield images were used to normalize CTG measurements for each well. Total surface areas (tSA) outputted from the machine learning model were used for normalizing the plating variations. The measured CTG value of each well was then divided by these surface area ratios to determine the adjusted CTG values. These adjusted CTG values were used to generate drug response curves, e.g., viability curves for each drug condition.

For the live and dead cell dyes-based imaging assay, the integrated live cell dye (Calcein AM) and dead cell dye (Eth) signals for each segmented object were determined. To assess drug response at individual MOS level, the integrated intensities, or the ratios of Calcein AM/EtH, were shown on the scatter plot or histogram. The correlation of dose-dependent drug response with the median ratios of the integrated live/dead cell dye intensities from each well were computed and plotted.

Figure 4A:
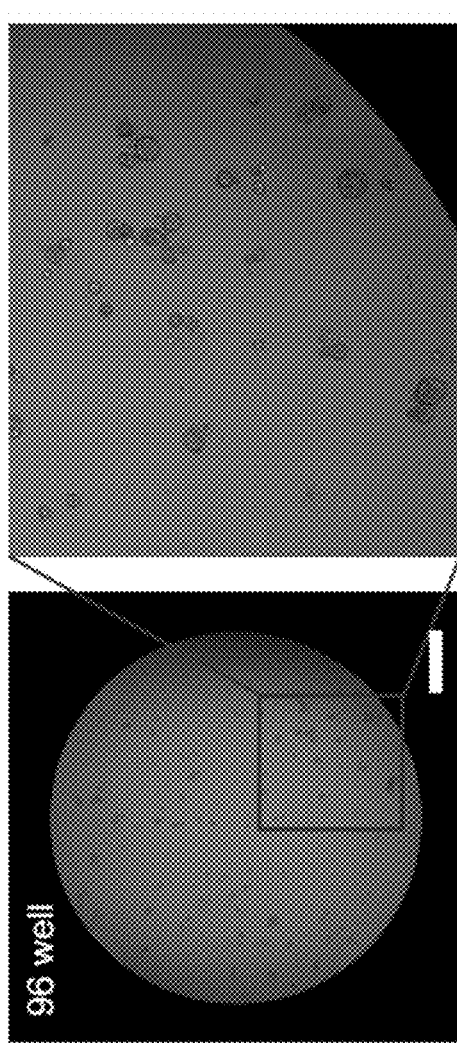
FIGS. 4A-4B illustrate example images of a whole well scanning (left panel) and a zoom-in view (right panel) showing identified MOS instances by a machine learning method.
Figure 4B:
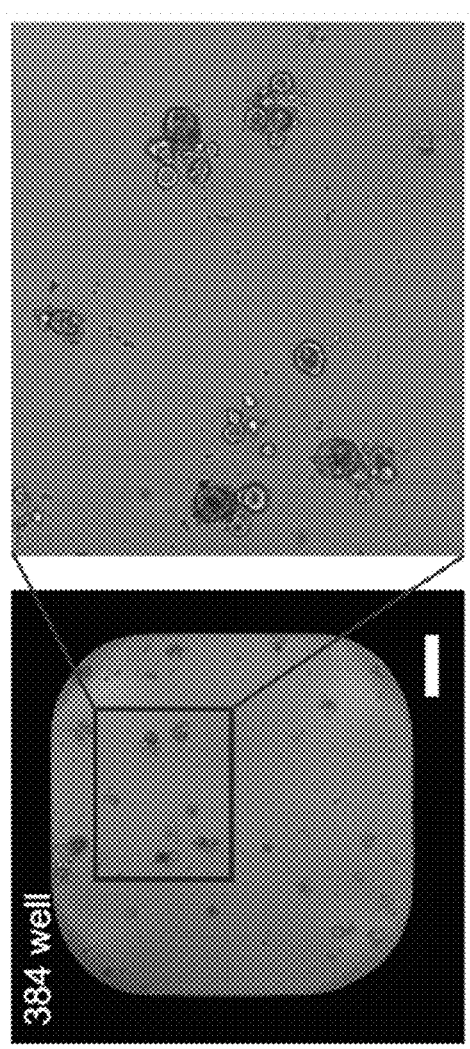

Example 1. MOS Coupled with a Machine Learning Enables a Normalization Approach for Improving the Robustness of Bulk Drug Assay Given the often-limited number and size heterogeneity of MOSs, e.g., organoids/tumorspheres derived from clinical primary tissue, significant well-to-well and plate-to-plate variations have been challenging for conventional drug response assays, e.g., bulk assays that measure metabolic activities such as intracellular ATP levels from a well level. Moreover, endpoint assays such as CTG are not able to assess growth kinetics, capture heterogeneity, distinguish cytotoxic vs. cytostatic effects, or delineate tumor cells from stromal cells, all of which are important for assessing clinical drug response. Unlike the multi-focal planes when growing bulk organoids in a BME dome, we noticed that most MOS were settled on the bottom of the microplate wells (e.g., 96 well, 384 well plates) and in the same focal plane after dispensing (FIGS. 4A-4B; scale bar of 1,000 μm), which therefore allowed us to quickly image each individual MOS without doing time-consuming multiple Z stack scans. We acquired all the images of the individual MOS (three channels) using Celigo imaging cytometer from a whole 96 well plate in about 5 minutes. A machine learning method was developed that leverages the implementation of Mask-RCNN to accurately segment MOSs from the acquired brightfield images (FIG. 3A) and output the sizes of MOSs and fluorescence intensities. Total surface area (tSA) outputted by the machine learning method was highly correlated with CTG luminescence signals detected in both a cystic model (FIG. 4C) and a dense colorectal cancer (CRC) MOS model (FIG. 4D).

We evaluated how the tSA could be used in normalizing the well-to-well plating variations when performing a drug assay. As shown in FIG. 3B, after normalizing the raw relative light unit (RLU) values of CTG assay with the Day 0 tSA (red curves), both the range error bars and R-squared of the adjusted CTG values were observed to be significantly improved, compared to the unnormalized blue curves, when these two models were treated with SN38, 5-FU, or Oxaliplatin (FIG. 3B), suggesting that image-based Day 0 tSA normalization strategy can overcome well-to-well plating variations. This improvement resulted in more robust and sensitive CTG-based drug assays.

Figure 3C:
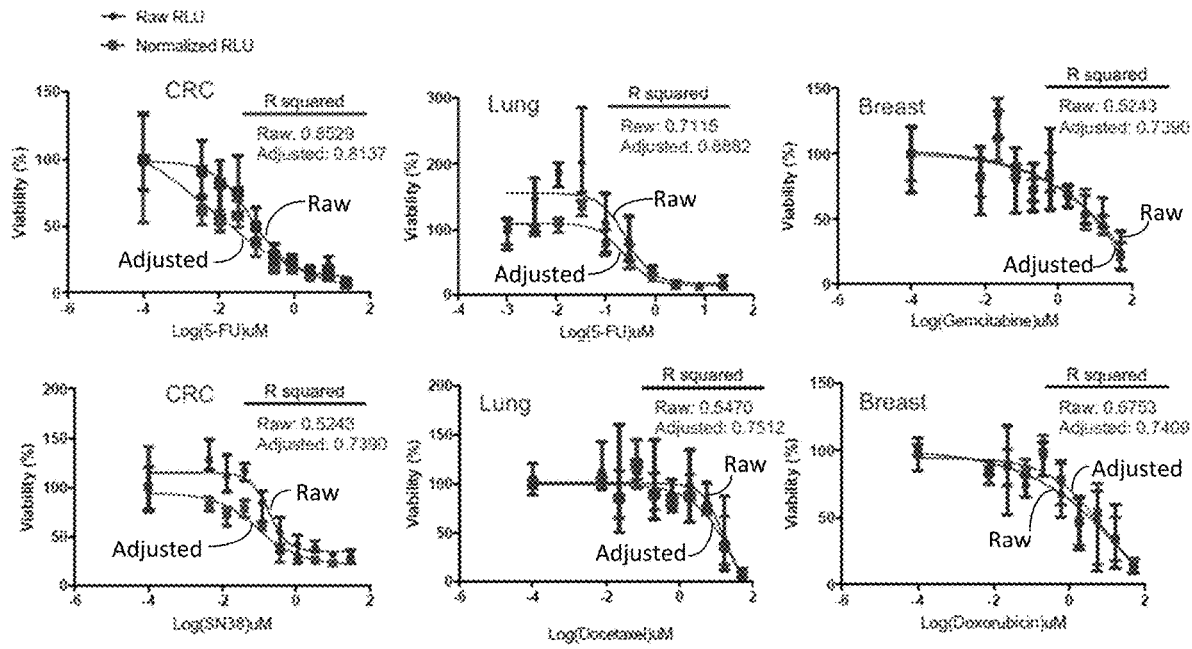
FIG. 3C illustrates example drug response curves of MOSs derived from lung, colorectal cancer (CRC), and breast cancer primary tissues before and after normalization.
Figure 3D:
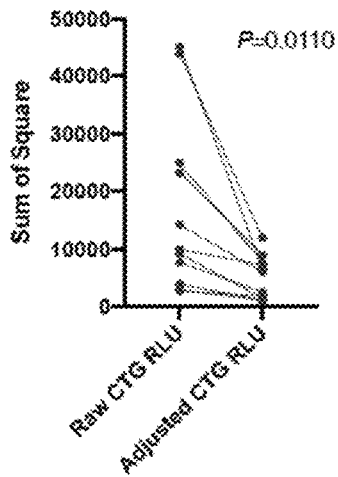
FIG. 3D illustrates a comparison between raw CellTiter-Glo (CTG) luminescent cell viability assay and adjusted CTG assay in measuring drug responses in MOSs.
Figure 4F:
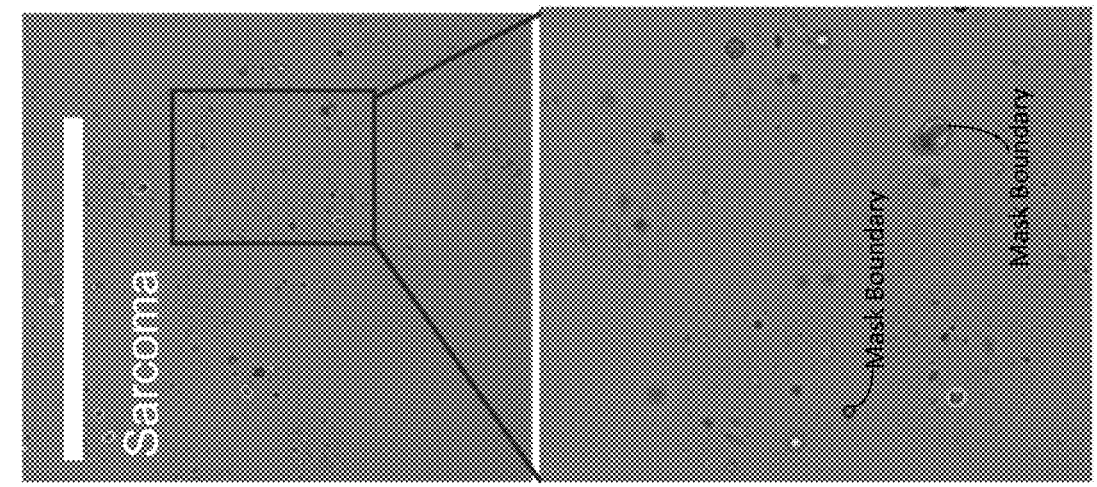
FIG. 4F illustrates an example image of MOSs derived from primary sarcoma tissue (top panel) and a zoom-in view (bottom panel) showing identified MOS instances by a machine learning method.
Figure 4E:
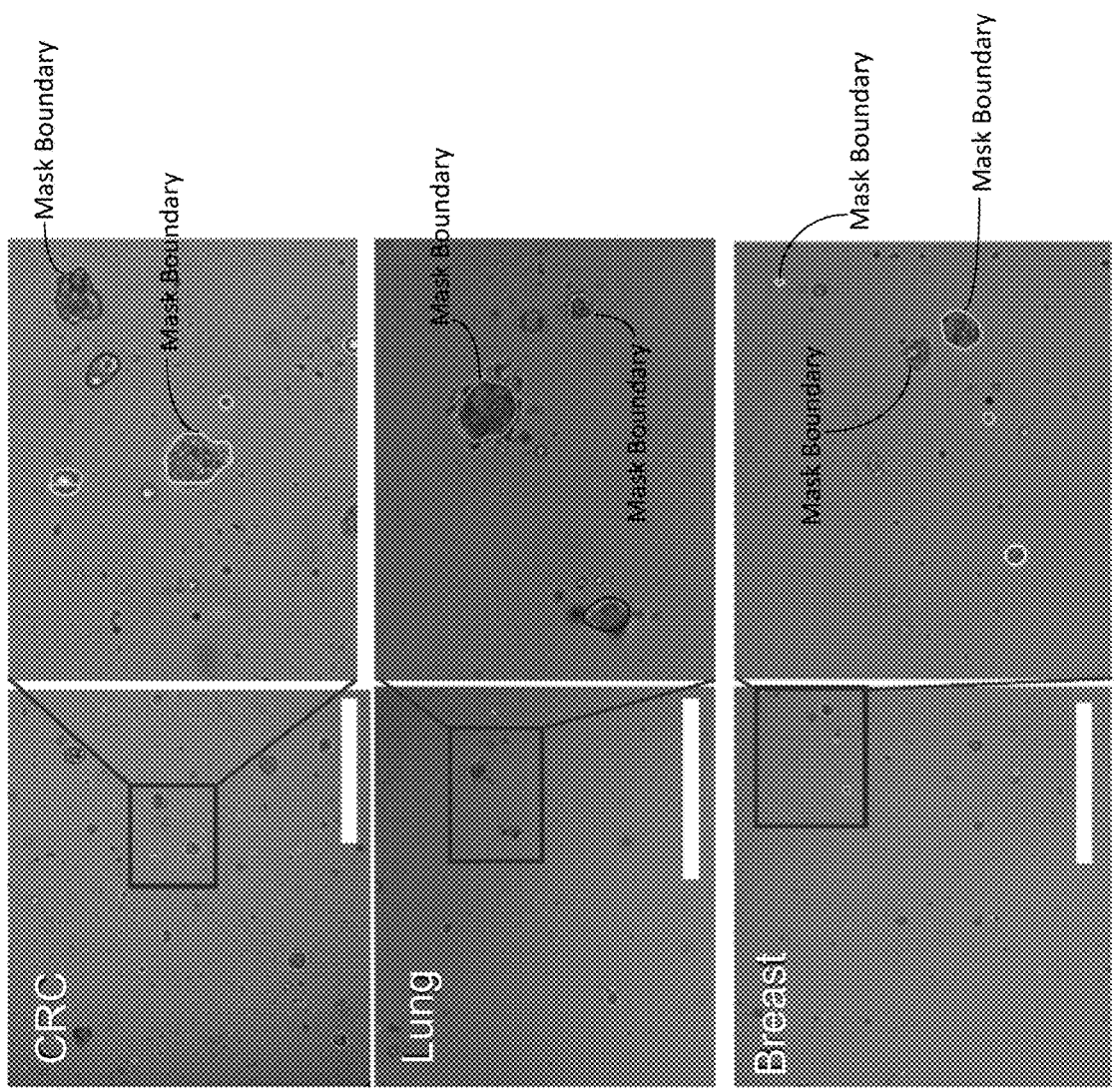
FIG. 4E illustrates example images of MOSs derived from colorectal cancer (CRC), lung, and breast tumor tissues (left panels) and zoom-in views (right panels) showing identified MOS instances by a machine learning method.

The tSA normalization was applied, based on the machine learning model, to three different types of primary tumors (CRC, lung, and breast) derived MOS models on P0 (FIG. 4E) after 4-7 days of being established from primary tissue digestion. In all three MOS models tested, we observed dose-dependent drug responses to chemotherapeutic agent treatments (blue curves, FIG. 3C). However, the variations of each drug concentration were significantly higher given the heterogeneous nature of establishment rates and size of MOS in each well. With the tSA normalization, a significant reduction of range error bars and increase of R-squared of the adjusted CTG results were observed (red curves, FIG. 3C). Additionally, the sum of square of the adjusted CTG values on both established PDO and primary tissue derived MOS were significantly decreased with the paired t-test two-tailed p-value of 0.011 (FIG. 3D).

Example 2. An Orthogonal Approach Combining a Machine Learning Method with Fluorescence Images to Differentiate Between Cytostatic and Cytotoxic Drug Effects and Captures Heterogeneous Drug Response at a Single Tumorsphere/Organoid Resolution To further increase the resolution and power of MOS drug assay pipeline, we developed an orthogonal approach by spiking a combination of live-cell (Calcein AM, CAM) and dead-cell (Ethidium Homodimer II, EtH) dyes (FIG. 5A; scale bar of 200 μm) into the drug assay plates prior to performing the CTG assay. We were able to quantitatively measure the integrated intensities of the CAM and EtH dyes in addition to MOS sizes. We observed that the sizes of CRC #5 (top panel) were decreased in response to Erlotinib (an EGFR inhibitor) and SN38 treatments. However, the ratios of CAM/EtH dye integrated intensities were only decreased in the wells treated with SN38 (FIG. 5A, top panel) but not in Erlotinib treated conditions, suggesting that Erlotinib triggered a cytostatic effect but SN38 triggered a cytotoxic effect on this model. Similar changes of the ratios of CAM/EtH dye integrated intensities were observed in another model, CRC #6, when treated with Erlotinib and SN38; however, there was no obvious decrease of the sizes of CRC #6 model when treated with Erlotinib, indicating that CRC #6 is resistant to EGFR inhibition.

Figure 5B:
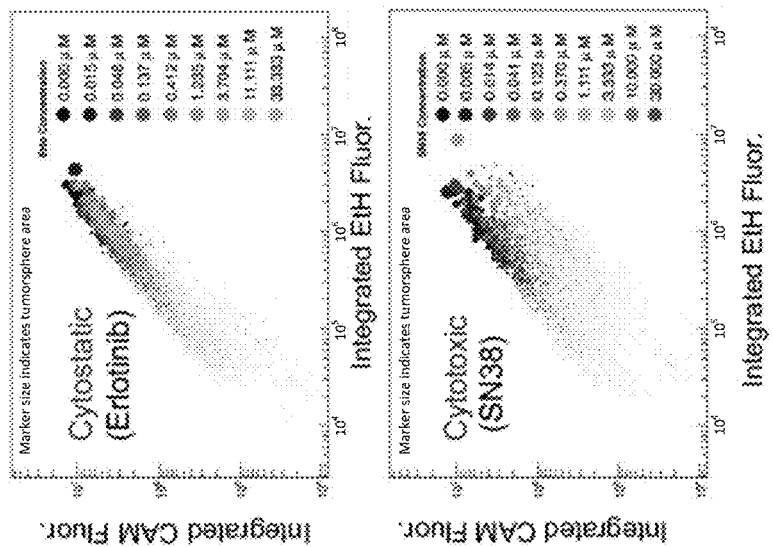
FIG. 5B illustrates example differential drug responses across varying doses of cytostatic or cytotoxic drugs.

Using the machine learning system, different readouts of an individual MOS were automatically captured including size, integrated live dye, and integrated dead cell dye signals, when the drug treatments were applied (FIG. 5B, FIG. 5D) on top of CTG assay. In FIG. 5B, the size of each dot indicates the relative surface area of the individual segmented MOS instance.

Figure 5A:
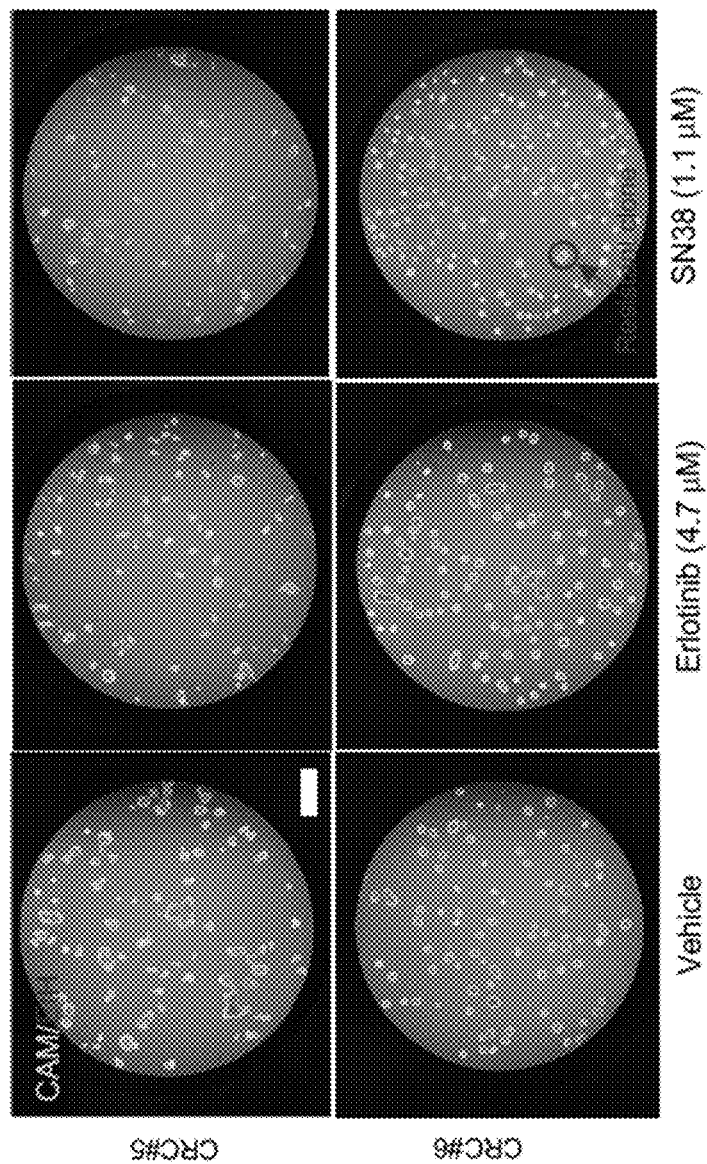
FIG. 5A illustrates example images of two CRC models treated with vehicle, Erlotinib, or SN38, co-stained with live cell dye (CAM) and dead cell dye (EtH).
Figures 5C, 5D:
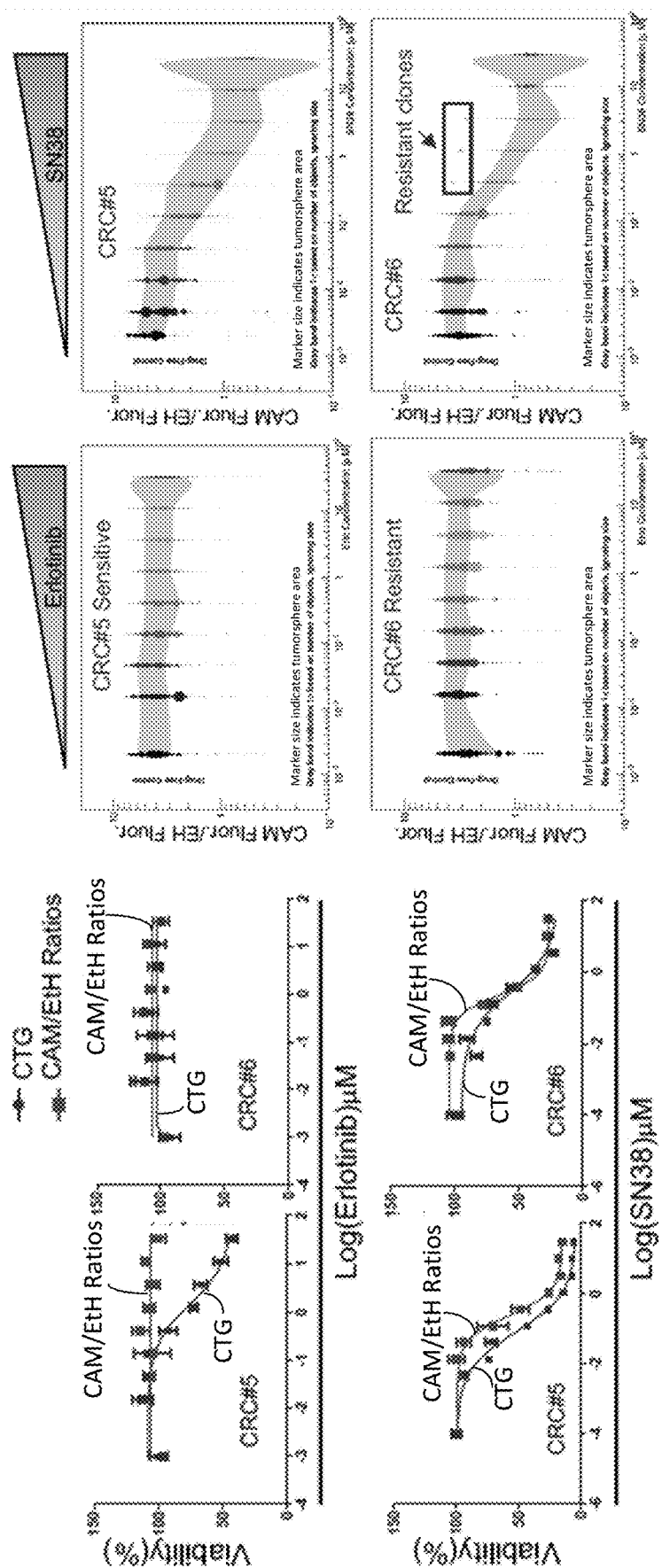
FIG. 5C illustrates example drug response curves of two CRC MOS models treated with Erlotinib or SN38.
FIG. 5D illustrates example dose-dependent changes of the ratios of CAM/EtH dye integrated intensities of two CRC models treated with Erlotinib or SN38.

We observed the drug response curves of two CRC MOS models treated with Erlotinib or SN38. In FIG. 5C, blue curves were plotted based on CTG assay, and red curves were plotted based on the median ratios of CAM/Eth dye integrated intensities. Based on the median values from the CAM/EtH dye ratios of each individual MOS, we observed a comparable dose-dependent drug responses (FIG. 5C, bottom panel) of these two CRC models when treated with SN38 as compared to CTG based assay. However, there was a divergence between CTG plot and CAM/EtH ratio plot in CRC #5, thus confirming that Erlotinib treatment triggers the cytostatic but not the cytotoxic effect on CRC #5. We also identified the drug resistant clones in CRC #6 model treated with SN38 as shown in FIG. 5A and FIG. 5D. In FIG. 5D, the red rectangle indicates the drug resistant clones identified in the CRC #6 treated with SN38. The x-axis indicates the range of drug concentrations. The size of each dot indicates the relative surface area of the individual segmented object. Gray band indicates 1σ based on number of objects, ignoring size.

Figures 5E, 5F:
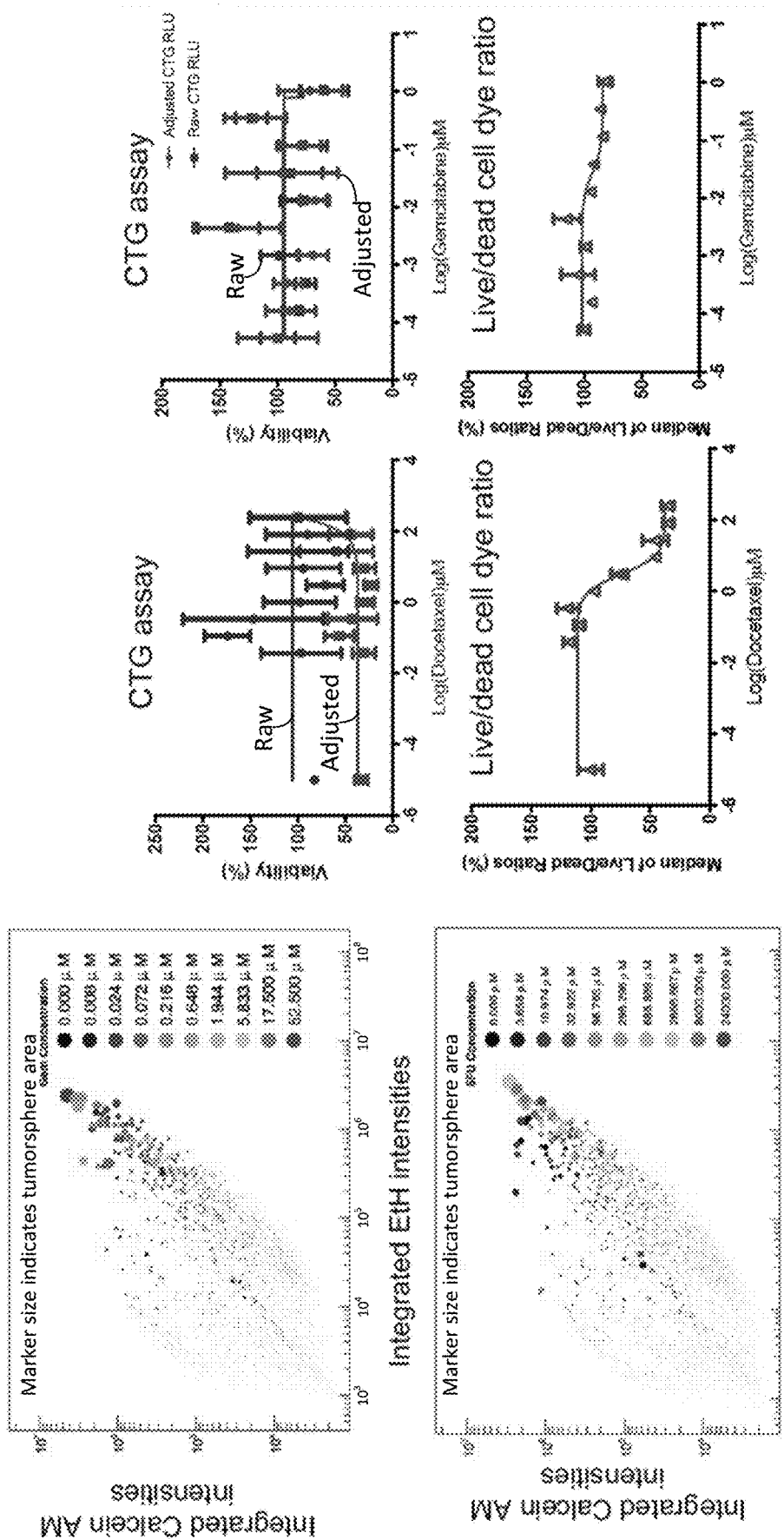
FIG. 5E illustrates example differential drug responses of individual MOSs derived from a primary lung tumor.
FIG. 5F illustrates comparison of drug response curves measured by CTG assay (top panel) and drug response curves measured by median of live cell dye and dead cell dye ratios in MOSs derived from a sarcoma primary tissue (bottom panel).

Furthermore, we observed that the drug responses were more heterogenous in the primary tissue derived MOS (FIG. 5E) as compared to the established models CRC #5 and CRC #6. Therefore, the CAM/EtH cell dye ratios coupling with size measurement as well as CTG assay allowed us to differentiate the cytotoxic vs. cytostatic drug effects.

Moreover, in a sarcoma cancer MOS (FIG. 4F) treated with Docetaxel or Gemcitabine on Day 7 after establishment, the bulk CTG readouts, raw CTG or adjusted CTG, were not able to provide any meaningful dose-dependent drug response curves due to limited tumorsphere number, notable resident stromal cells in the MOS droplet, and well-to-well variation. Conversely, the median values from the live/dead cell ratios detected and measured from the same well showed a clear dose-dependent drug response to the treatment of Docetaxel (FIG. 5F, bottom panel) and a less sensitive response to Gemcitabine treatment. The imaging-based MOS drug assay allowed further delineating MOS 3D structures from individual stromal cells by overcoming fundamental limits of bulk assays, e.g., cell number, well-to-well variation, heterogeneity, and signal-to-noise ratio.

OTHER EMBODIMENTS

It is to be understood that although various illustrative embodiments are described above, the foregoing description is intended to illustrate and not limit the scope of the disclosure, which is defined by the scope of the appended claims Other aspects, advantages, and modifications are within the scope of the following claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A system comprising:
   a well plate configured to contain a plurality of substantially spherical droplets, each of the droplets comprising a base material and one or more three-dimensional cell aggregates;
   an input device configured to obtain image data of the well plate when the plurality of substantially spherical droplets are present in the well plate;
   one or more processing devices; and
   one or more storage devices storing instructions that, when executed by the one or more processing devices, cause the one or more processing devices to perform operations comprising:
      implementing a machine learning model to identify instances of at least some of the plurality of substantially spherical droplets in the image data,
      obtaining (i) one or more indications of each instance of the substantially spherical droplets and (ii) one or more attributes of each instance of the substantially spherical droplets,
      normalizing, based on the one or more indications and the one or more attributes, a well-to-well variation in the well plate, and
      determining, based on the one or more indications outputted by the machine learning model, a fluorescence activity of one or more instances of the substantially spherical droplets,
         wherein the fluorescence activity comprises a live cell dye signal and a dead cell dye signal of the one or more instances of the substantially spherical droplets, and
         wherein determining the fluorescence activity of the one or more instances of the substantially spherical droplets comprises performing a logical operation between the image data and the one or more indications.

2. The system of claim 1, wherein the operations comprise determining a cell viability in the normalized well plate based on a drug assay performed on the plurality of substantially spherical droplets, wherein the drug assay measures the cell viability in response to a drug treatment to a given well in the well plate.

3. The system of claim 1, whe, rein the substantially spherical droplets are derived from a patient-derived tissue sample.

4. The system of claim 3, wherein the patient-derived tissue sample comprises a biopsy sample from a metastatic tumor.

5. The system of claim 3, wherein the patient-derived tissue sample comprises a clinical tumor sample comprising both cancer cells and stromal cells.

6. The system of claim 1, wherein the image data comprise a brightfield image and a fluorescence image of the well plate.

7. The system of claim 1, wherein the one or more indications comprise a visual representation of each instance of the substantially spherical droplets in the image data, and wherein the system further comprises a user device with a display, the user device configured to present the visual representation of each instance of the substantially spherical droplets on a user interface.

8. The system of claim 1, wherein determining the fluorescence activity of the one or more instances of the substantially spherical droplets comprises:
   iteratively adjusting the one or more indications outputted from the machine learning model such that the dead cell dye signal is captured; and
   outputting, based on the adjusted one or more indications, the fluorescence activity of the one or more instances of the substantially spherical droplets.

9. The system of claim 1, wherein the one or more attributes of each instance of the substantially spherical droplets comprise a total surface area of each instance, the live cell dye signal, and the dead cell dye signal.

10. The system of claim 1, wherein normalizing the well-to-well variation in the well plate comprises:
    obtaining a total surface area of each instance of the substantially spherical droplets in the well plate, wherein the total surface area is correlated with a level of adenosine triphosphate (ATP) of each instance of the substantially spherical droplets;
    obtaining, for each well of the well plate, a cell viability in response to a drug treatment; and
    adjusting, based on the total surface area, respective cell viability across a plurality of wells in the well plate.

11. The system of claim 1, wherein the operations comprise determining an integrated cell viability in a given well in the well plate, the given well being treated with a live cell dye corresponding to the live cell dye signal and a dead cell dye corresponding to the dead cell dye signal prior to performance of a drug assay on a plurality of substantially spherical droplets in the given well.

12. The system of claim 11, wherein the drug assay comprises a CellTiter-Glo (CTG) luminescent cell viability assay.

13. The system of claim 11, wherein the live cell dye comprises a calcein-AM and a mitotracker viewer.

14. The system of claim 11, wherein the dead cell dye comprises an ethidium homodimer-2 and a fluorescent conjugated annexin V.

15. The system of claim 11, wherein the operations comprise determining, based on the integrated cell viability, cytotoxic or cytostatic drug responses.

16. The system of claim 1, wherein the operations comprise filtering out stromal cells and non-tumorspheres in the one or more indications in response to applying a size filter to the one or more indications, wherein the size filter removes cells under a pre-defined size from the one or more indications.

17. The system of claim 1, wherein one or more wells in the well plate are treated with a stain that non-specifically binds to organic tissue and the base material of the plurality of substantially spherical droplets.

18. The system of claim 1, wherein the input device is configured to obtain the image data of the well plate at a single focal plane or using a two-dimensional projection of three-dimensional confocal microscopy Z-stacks.

19. The system of claim 1, wherein obtaining the one or more indications of each instance of the substantially spherical droplets in the image data comprises generating a corresponding mask represented using a Fourier series representation, wherein the Fourier series representation is generated based on coefficients output by the machine learning model.

20. The system of claim 19, wherein the machine learning model is trained using images that include labeled droplet instances, the labeled droplet instances being labeled using a pre-trained neural network configured to generate image instance segmentation masks.

21. The system of claim 20, wherein the images that include the labeled droplet instances are generated from unlabeled images, and wherein the unlabeled images are pre-processed using (i) a mathematical transformation that enhances fluorescence corresponding to stained droplets present in the unlabeled images, (ii) a mathematical morphology operation that enhances disk-like objects that are within a defined range of sizes, and (iii) an image-resizing operation.

22. A system comprising:
one or more processing devices and one or more storage devices storing instructions that, when executed by the one or more processing devices, cause the one or more processing devices to perform operations comprising:
obtaining a first input including brightfield image data and fluorescence image data for each droplet of a plurality of substantially spherical droplets, each of the droplets comprising a base material and one or more three-dimensional cell aggregates;
obtaining a second input indicative of a ground-truth label representing each droplet of the plurality of substantially spherical droplets; and
training, by using a set of the first and the second inputs across the plurality of substantially spherical droplets, a machine learning model configured to identify (i) each instance of the substantially spherical droplets and (ii) one or more attributes of each instance of the substantially spherical droplets.

23. The system of claim 22, wherein the operations comprise applying binarization to the fluorescence image data in response to determining that a saturation level of the fluorescence image data does not meet a pre-defined threshold.

24. The system of claim 22, wherein obtaining the second input indicative of the ground-truth label representing each droplet comprises generating the ground-truth label by applying, to one or more unlabeled images, a pre-trained neural network configured to generate image segmentation masks.

25. The system of claim 24, wherein the operations comprise:
applying, to the one or more unlabeled images, (i) a mathematical transformation that enhances fluorescence corresponding to stained droplets present in the unlabeled images, (ii) a mathematical morphology operation that enhances disk-like objects that are within a defined range of sizes, and (iii) an image-resizing operation.

26. The system of claim 22, wherein training the machine learning model comprises training the machine learning model to output coefficients for a Fourier series representation of one or more image segmentation masks corresponding to the substantially spherical droplets.

27. The system of claim 22, wherein the plurality of substantially spherical droplets are treated with a stain that non-specifically binds to organic tissue and the base material of the plurality of substantially spherical droplets.

28. The system of claim 27, wherein the plurality of substantially spherical droplets are treated prior to obtaining the first input including brightfield image data and fluorescence image data.

29. A system comprising:
a well plate configured to contain a plurality of substantially spherical droplets, each of the droplets comprising a base material and one or more three-dimensional cell aggregates;
an input device configured to obtain image data of the well plate when the plurality of substantially spherical droplets are present in the well plate;
one or more processing devices; and
one or more storage devices storing instructions that, when executed by the one or more processing devices, cause the one or more processing devices to perform operations comprising:
implementing a machine learning model to identify instances of at least some of the plurality of substantially spherical droplets in the image data,
obtaining (i) one or more indications of each instance of the substantially spherical droplets and (ii) one or more attributes of each instance of the substantially spherical droplets, and
normalizing, based on the one or more indications and the one or more attributes, a well-to-well variation in the well plate, and
determining, based on the one or more indications outputted by the machine learning model, a fluorescence activity of one or more instances of the substantially spherical droplets,
wherein the fluorescence activity comprises a live cell dye signal and a dead cell dye signal of the one or more instances of the substantially spherical droplets, and
wherein determining the fluorescence activity of the one or more instances of the substantially spherical droplets comprises (i) iteratively adjusting the indications outputted from the machine learning model such that the dead cell dye signal is captured and (ii) outputting, based on the adjusted indications, the fluorescence activity of the one or more instances of the substantially spherical droplets.

30. A system comprising:
a well plate configured to contain a plurality of substantially spherical droplets, each of the droplets comprising a base material and one or more three-dimensional cell aggregates;

an input device configured to obtain image data of the well plate when the plurality of substantially spherical droplets are present in the well plate;

one or more processing devices; and one or more storage devices storing instructions that, when executed by the one or more processing devices, cause the one or more processing devices to perform operations comprising:

implementing a machine learning model to identify instances of at least some of the plurality of substantially spherical droplets in the image data, obtaining (i) one or more indications of each instance of the substantially spherical droplets and (ii) one or more attributes of each instance of the substantially spherical droplets, and normalizing, based on the one or more indications and the one or more attributes, a well-to-well variation in the well plate, wherein normalizing the well-to-well variation in the well plate comprises:

obtaining a total surface area of each instance of the substantially spherical droplets in the well plate, wherein the total surface area is correlated with a level of adenosine triphosphate (ATP) of each instance of the substantially spherical droplets;

obtaining, for each well of the well plate, a cell viability in response to a drug treatment; and adjusting, based on the total surface area, respective cell viability across a plurality of wells in the well plate.

31. A system comprising:

a well plate configured to contain a plurality of substantially spherical droplets, each of the droplets comprising a base material and one or more three-dimensional cell aggregates;

an input device configured to obtain image data of the well plate when the plurality of substantially spherical droplets are present in the well plate;

one or more processing devices; and one or more storage devices storing instructions that, when executed by the one or more processing devices, cause the one or more processing devices to perform operations comprising:

implementing a machine learning model to identify instances of at least some of the plurality of substantially spherical droplets in the image data, obtaining (i) one or more indications of each instance of the substantially spherical droplets and (ii) one or more attributes of each instance of the substantially spherical droplets, and normalizing, based on the one or more indications and the one or more attributes, a well-to-well variation in the well plate, wherein obtaining the indications of each instance of the substantially spherical droplets in the image data comprises generating a corresponding mask represented using a Fourier series representation, wherein the Fourier series representation is generated based on coefficients output by the machine learning model, and wherein the machine learning model is trained using images that include labeled droplet instances, the labeled droplet instances being labeled using a pre-trained neural network configured to generate image instance segmentation masks.

\* \* \* \* \*

UNITED STATES PATENT AND TRADEMARK OFFICE
CERTIFICATE OF CORRECTION

PATENT NO. : 12,100,151 B2
APPLICATION NO. : 18/419291
DATED : September 24, 2024
INVENTOR(S) : Xiling Shen et al.

It is certified that error appears in the above-identified patent and that said Letters Patent is hereby corrected as shown below:

In the Claims

Column 20, Line 4, In Claim 3, delete "whe, rein" and insert -- wherein --.

Signed and Sealed this
Twelfth Day of November, 2024

Katherine Kelly Vidal
*Director of the United States Patent and Trademark Office*